United States Patent [19]

Molloy et al.

[11] Patent Number: 4,528,177

[45] Date of Patent: * Jul. 9, 1985

[54] IMAGING AGENTS AND METHOD

[75] Inventors: Bryan B. Molloy, North Salem; Mitchell I. Steinberg, Indianapolis, both of Ind.

[73] Assignee: Eli Lilly and Company, Indianapolis, Ind.

[*] Notice: The portion of the term of this patent subsequent to Sep. 15, 1998 has been disclaimed.

[21] Appl. No.: 435,137

[22] Filed: Oct. 18, 1982

[51] Int. Cl.$^3$ .................... A61K 43/00; A61K 49/00
[52] U.S. Cl. .................................... 424/1.1; 424/9; 564/289
[58] Field of Search ............... 564/289; 424/1.1, 9

[56] References Cited

U.S. PATENT DOCUMENTS

| 4,048,297 | 9/1977 | Counsell et al. | 424/1 |
| 4,279,887 | 7/1981 | Baldwin et al. | 424/1.1 |
| 4,289,787 | 9/1981 | Molloy et al. | 424/329 |
| 4,308,249 | 12/1981 | Frank et al. | 424/1.1 |
| 4,363,793 | 12/1982 | Blau et al. | 424/1.1 |

FOREIGN PATENT DOCUMENTS 0011858 6/1980 European Pat. Off. .

OTHER PUBLICATIONS

"The Design of Organ-Imaging Radiopharmaceuticals", Counsell and Ice, Chapter 4, pp. 172-194 in Drug Design, E. J. Arien, vol. VI, Academic Press, N.Y., 1975.
Hamilton, J. Nucl. Med., 20, 1201-1205 (1979).
Burns et al., J. Nucl. Med., 21, 875-879 (1980).
Counsell et al., J. Med. Chem., 16, 1038-1040 (1973).
Korn et al., J. Pharm. Sci., 69, 1010-1013 (1980).
Dannals et al., J. Pharm. Sci., 70, 439-442 (1981).
Kline et al., J. Nucl. Med., 22, 129-132 (1981).
Lindstrom et al., J. Pharm. & Exp. Thera., 221, 584-589 (1982).

Primary Examiner—Christine M. Nucker
Attorney, Agent, or Firm—Charles W. Ashbrook; Arthur R. Whale

[57] ABSTRACT

Radioiodine containing phenylbutylammonium salts are valuable imaging agents, particularly for the heart.

9 Claims, No Drawings

IMAGING AGENTS AND METHOD

BACKGROUND OF THE INVENTION

The use of radioiodine to label organic compounds for use in diagnostic nuclear medicine is known. For example, Blan et al., in *Int. J. App. Radiat. Isoropes*, 3, pp. 217–225 (1958), described the use of p-iodobenzoyl chloride (I-131) to label antibiotics for the determination of in vivo protein distribution. Bolton and Hunter, *Biochem. J.*, 133, pp. 529–539 (1973), reported that the N-hydroxysuccinimide ester of 3-(4-hydroxyphenyl)-propionic acid-$^{125}$I is useful to radio-label proteins. Smith, in U.S. Pat. No. 3,979,506, described imido esters of radionuclide-substituted hydroxy or alkoxy phenyls wherein the nuclide can be I-125. Wieland et al., in *J. Nucl. Med.*, 22, 358–364 (1981) described the use of [$^{123}$I] and [$^{131}$I] metaiodobenzylguanidine to image primate adrenal medulla. Kline et al. reported on the myocardial imaging in man with [$^{123}$I] meta-iodobenzylguanidine; *J. Nucl. Med.*, 22, 129–132 (1981).

An excellent review of the theory and practice of nuclear medicine is found in "Nuclear Cardiology For Clinicians" edited by Soin and Brooks, Futura Publishing Company, Mount Kisco, N.Y., 1980. A survey of radiopharmaceuticals and their use in nuclear medicine was written by Cornsell and Ice in "Drug Design", Vol VI, E. J. Ariens, Ed., Academic Press, New York, N.Y. 1975, Chapter 4.

Molloy et al., in U.S. Pat. No. 4,289,787, disclose a new group of quaternary ammonium compounds that are useful in treating cardiac arrhythmias and prolonging the action potential duration of cardiac tissue. Of particular interest with the group is the compound N,N-diethyl-N-n-heptyl-4-(4-chlorophenyl)butylammonium phosphate, now generically referred to as clofilium.

It has now been found that clofilium, and compounds similar in structure to clofilium, are particularly effective in binding to certain animal tissue, especially cardiac tissue. Accordingly, it is an object of this invention to provide certain quaternary ammonium compounds bearing a radioiodine atom as a label. Such compounds are useful as imaging agents, particularly cardiac imaging agents.

SUMMARY OF THE INVENTION

This invention concerns radioiodine labelled organic compounds that are useful as imaging agents. The invention more particularly provides a radioiodine containing phenylbutyl ammonium compound of the formula

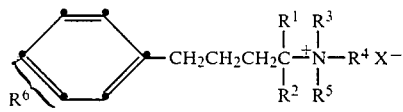

wherein:
$R^1$ is hydrogen or $C_1$–$C_2$ alkyl;
$R^2$ is hydrogen or $C_1$–$C_3$ alkyl;
$R^3$ is $C_1$–$C_4$ alkyl or phenyl-$C_1$–$C_4$ alkyl;
$R^4$ is $C_1$–$C_8$ alkyl;
$R^5$ is $C_6$–$C_{10}$ alkyl;
$R^6$ is a radioiodine atom; and
X is a therapeutically acceptable anion such as chloro, bromo, iodo, phosphate, para-toluenesulfonate, acetate, hydroxide or methanesulfonate.

Preferred compounds are those of the above formula wherein $R^6$ is I-123, I-125 or I-131, especially I-123.

Additionally preferred are compounds wherein $R^1$ and $R^2$ both are hydrogen, and $R^3$ and $R^4$ both are ethyl, and $R^5$ is a normal-$C_6$–$C_{10}$ alkyl group.

The most preferred compounds according to this invention are those wherein $R^1$ and $R^2$ both are hydrogen, $R^3$ and $R^4$ both are ethyl, $R^5$ is n-heptyl, $R^6$ is para$^{123}$I, and X$^-$ is bromide, phosphate or para-toluenesulfonate.

A further embodiment of this invention is a method of imaging cardiac tissue comprising administering an effective amount of a compound as defined above, and scanning the cardiac region with a scintiscanning means.

DETAILED DESCRIPTION OF THE INVENTION

The compounds provided by this invention can be prepared by metathetic exchange of an iodophenylalkyl quaternary ammonium compound of U.S. Pat. No. 4,289,787 with a gamma-emitting radioisotope of iodine. $R^6$ in the above formula defines a radioisotope of iodine, and includes I-123, I-125 and I-131. The practice of this invention is preferably carried out employing compounds wherein $R^6$ is I-123. Ideally, $R^6$ is attached at the 4-position of the phenyl ring.

The exchange radiolabeling process can be carried out by simply reacting an inorganic salt of a radioisotope of iodine, for example an alkali metal salt such as $^{123}$INa, $^{123}$IK, $^{125}$ILi, $^{131}$INa or $^{123}$ILi, with a cold halo, preferable iodo, compound of the formula

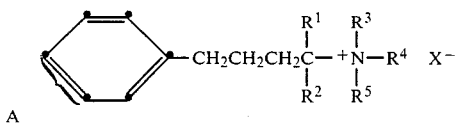

wherein $R^1$, $R^2$, $R^3$, $R^4$, $R^5$ and X$^-$ are as defined above, and A is stable halo such as chloro, bromo or iodo, and not a radioisotope. These cold halo compounds are described in U.S. Pat. No. 4,289,787, which is incorporated herein by reference for its teaching of such compounds and their synthesis. The exchange reaction generally is carried out by combining approximately equimolar quantities of the cold halo compound with the alkali metal radioiodo salt. An excess of the alkali metal salt can be employed if desired. For example, $^{123}$INa is a typical reactant employed to prepare compounds of this invention and routinely is used in about 0.1 to about 10.0 molar excess relative to the cold halo starting material. The reaction generally is carried out in an unreactive organic solvent, and lower alkyl alcohols such as methanol, ethanol, isopropanol and n-butanol are typical. Other commonly employed solvents include ethyl acetate, dioxane, dichloromethane, benzene, tetrahydrofuran, N,N-dimethylformamide, and the like.

The exchange reaction generally is conducted at a temperature of about 20° to about 100° C., and at such temperature is usually substantially complete within about 0.5 to about 2 hours. Longer reaction times do not appear detrimental and can be employed if desired, although all such reactions should be terminated as soon as possible due to a comparatively short half-life of the iodine radioisotopes particularly I-123. For example, the half-life of I-123 is 13.3 hours; of I-125, 60 days; and of I-131, 8.05 days. Upon completion of the exchange reaction, the compound of this invention is conveniently isolated by filtering the reaction mixture, for instance through a silver chloride impregnated filter to remove any unexchanged radioiodine, and then removing the reaction solvent, for instance by evaporation under reduced pressure. The radiolabelled compound thus produced can be purified further if desired by routine methods such as crystallization, chromatography and the like.

The radiolabelled compounds of the invention can alternatively be prepared by alkylating an already labelled phenylbutylamine, for example a tertiary amine of the formula

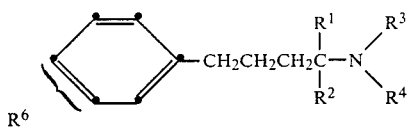

wherein $R^1$, $R^2$, $R^3$, $R^4$ and $R^6$ are as defined above. This alternative process is carried out by first radiolabelling a halophenylbutylamine, for instance by an exchange reaction similar to that described above. The radiolabelled tertiary amine of the above formula is then reacted with an $R^5$ alkylating agent, for example an alkyl halide such as n-heptyl bromide or n-decyl chloride. Such alkylation reaction is generally carried out in an unreactive organic solvent such as dichloromethane or benzene, and the product that is formed is a quaternary ammonium salt that characteristically exists as a crystalline solid. Such product normally crystallizes directly out of the reaction solvent and normally needs no further purification.

Typical radioiodine-containing compounds that can be prepared by the methods described above and that are provided by this invention are illustrated in the following table.

As noted above, the radioiodine labelled compounds of this invention rapidly localize in the myocardium and are thus useful for imaging the heart of mammals, particularly humans. The compounds also localize in other organs, for example the pancreas, kidney, adrenal, salivary gland and thyroid, and can therefore be employed for the imaging of these organs. It has been found, however, that the compounds are retained in the myocardium for a much longer period of time than in other organs, and accordingly are of particular importance in the imaging of the heart.

In general, an amount of a compound of this invention sufficient to permit the taking of scintiphotos will accumulate in cardiac tissue within about fifteen to thirty minutes following normal dosing. The compounds remain significantly bound to the myocardium well beyond seventy-two hours after dosing so that scintiphotos can be taken at anytime within such extended periods. The particular time for taking such scintiphotos or scintigrams will be governed primarily by the activity of the particular radioisotope of iodine present in the administered compound. Generally, the scintiphotos will be taken within about one to two hours following dosing of a preferred iodine-123 labelled compound, since iodine-123 has a comparatively short half-life.

The radioiodinated compounds of this invention can be administered in the form of pharmaceutical formulations, which comprise a further embodiment of this invention. Formulations can be prepared for convenient oral or parenteral administration, including the intravenous and intramuscular routes. The formulations typically will comprise from about 1 to about 80 percent by weight of radioiodinated compound, together with a conventional pharmaceutical carrier, excipient or diluent. Commonly used carriers and diluents include ethanol, saline, lactose, sucrose, starch powder, polyvinylpyrrolidine, cellulose, sodium benzoate and the like. Such formulations can be molded into tablets or encapsulated into gelatin capsules for convenient oral admin-

| $R^1$ | $R^2$ | $R^3$ | $R^4$ | $R^5$ | $R^6$ | $X^-$ |
|---|---|---|---|---|---|---|
| H | H | ethyl | ethyl | n-heptyl | 4-$^{123}$I | HPO$_4$ |
| H | H | methyl | ethyl | n-heptyl | 3-$^{125}$I | Br |
| H | methyl | ethyl | n-pentyl | n-hexyl | 3-$^{123}$I | 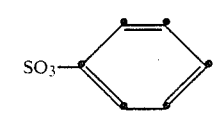 |
| H | ethyl | ethyl | n-propyl | n-hexyl | 4-$^{131}$I | Cl |
| methyl | methyl | methyl | ethyl | n-octyl | 4-$^{123}$I | 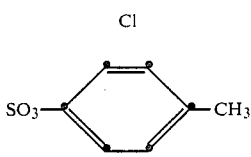 |
| H | H | ethyl | ethyl | isodecyl | 4-$^{125}$I | 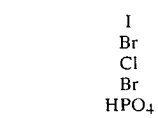 |
| H | H | 4-phenylbutyl | n-heptyl | 1-methylpentyl | 3-$^{131}$I | Br |
| H | H | methyl | methyl | n-decyl | 4-$^{123}$I | Cl |
| H | H | ethyl | ethyl | n-nonyl | 4-$^{123}$I | Br |
| methyl | H | methyl | n-propyl | n-octyl | 3-$^{131}$I | HPO$_4$ | istration, or can be dissolved or suspended in suitable diluents such as isotonic saline or aqueous dextrose for parenteral administration. The formulations are then administered at such a rate that the subject receives from about 1.0 to about 100 μg/kg of active ingredient.

The following examples further illustrate the present invention.

PREPARATION 1

N,N-Diethyl-N-n-heptyl-4-(4-iodophenyl)butylammonium bromide

A solution of 2.03 g. (6.3mM) of N-ethyl-N-n-heptyl-4(4-nitrophenyl)butylamine in 100 ml of 2B ethanol containing 1 g of 5% palladium on carbon was stirred under hydrogen at 50 p.s.i. for sixteen hours at 25° C. The reaction mixture was filtered and the solvent was removed by evaporation under reduced pressure to give 1.49 g of N-ethyl-N-n-heptyl-4-(4-aminophenyl)butylamine as an oil.

The oil thus formed was dissolved in 23 ml of 10% aqueous sulfuric acid and the solution was cooled to 0° C. and stirred while 1.8 ml of a 10% aqueous solution of sodium nitrate were added dropwise over five minutes. The reaction mixture was stirred at 0° C. for forty-five minutes following the addition, and then 2.0 g of copper bronze were added to the reaction mixture, followed by the addition of 1.79 g of sodium iodide in 2 ml of water. The reaction mixture was then heated to 85° C. for one hour. After cooling the mixture to room temperature, a mixture of 5N sodium hydroxide and diethyl ether was added, and the insolubles were removed by filtration. The organic layer was separated and extracted several times with 2N sulfuric acid. The acidic extracts were combined, made alkaline, and the alkaline solution was extracted with fresh diethyl ether. The organic layer was separated, washed with water, dried, and the solvent was removed by evaporation to give 1.45 g of N-ethyl-N-n-heptyl-4-(4-iodophenyl)butylamine.

The compound thus formed was reacted with ethyl bromide to give, following crystallization from ethyl acetate and acetone, N,N-diethyl-N-n-heptyl-4-(4-iodophenyl)butylammonium bromide.

Analysis calc.: for $C_{21}H_{37}BrIN$: Theory: C, 49.42; H, 7.31; N, 2.74; I, 24.87; Br, 15.66. Found: C, 49.26; H, 7.07; N, 2.61; I, 24.94; Br, 15.81.

EXAMPLE 1

N,N-Diethyl-N-n-heptyl-4-(4-[123]Iodophenyl)butylammonium bromide

A solution of N,N-diethyl-N-n-heptyl-4-(4-iodophenyl)butylammonium bromide (cold iodo substituted compound from Preparation 1) in ethanol containing excess sodium iodide I-123 is heated for one to two hours in a sealed vessel. The solution is then cooled and the solvent is removed by evaporation to provide N,N-diethyl-N-n-heptyl-4-(4-[123]Iodophenyl)butylammonium bromide.

EXAMPLE 2

The ability of compounds of the invention to selectively bind to animal organs was established indirectly by analyzing the disposition of $^{14}C$-clofilium when administered to rats and dogs. The test compound, N-($^{14}C$ethyl)-N-ethyl-N-n-heptyl-4-(4-chlorophenyl)butylammonium phosphate, was prepared by first reacting [$^{14}C$]acetyl chloride with N-n-heptyl-4-(4-chlorophenyl)butyl amine in toluene to give N-($^{14}C$ acetyl)-N-n-heptyl-4-(4-chlorophenyl)butylamine. This amide was reduced by reaction with diborane in tetrahydrofuran to give N-($^{14}C$ ethyl)-N-n-heptyl-4-(4-chlorophenyl)-butylamine, which was reacted with ethyl bromide to give the corresponding quaternary bromide salt. The quaternary bromide salt was converted to the hydroxide salt by passage of an aqueous solution over a Bio-Rad AG 1-X-4 column. The hydroxide salt thus formed was converted to the phosphate salt by reaction with dilute phosphoric acid to provide, following crystallization from acetone-diethyl ether, N-($^{14}C$ ethyl)-N-ethyl-N-n-heptyl-4-(4-chlorophenyl)butylammonium phosphate, (8.4μ Ci/mg), m.p. 128°–130° C., having the structure

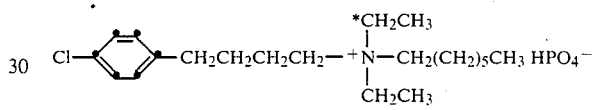

where * is $^{14}C$.

Tissue distribution studies were carried out employing male Wistar rats that were fasted 18 hours and then administered 5 mg/kg of $^{14}C$ labelled clofilium (8.4μ Ci/mg) by bolus injection into the lateral tail vein. After drug administration, animals were housed individually in metabolism cages and allowed access to food and water ad libitum. At various times following the dosing, randomly selected rats were anesthetized with ether and tissues were dissected, rinsed, blotted and weighed. Samples (80–150 mg) were digested in 0.2 ml of 70% aqueous perchloric acid and 0.4 ml of 30% aqueous hydrogen peroxide at 70° C. for two hours in scintillation vials. The samples were chilled and counted in PCS scintillation fluid. Rat carcasses were digested in 300 ml of ethanol and 50 g of potassium hydroxide. Aliquots (0.5 ml) of the whole body digest were combusted in a Packard Tri-Carb model 306 sample oxidizer and counted in duplicate.

The results of the distribution study are presented below in Table 1. Values in the Table represent the mean ±S.E.M. of four animals.

TABLE 1

| Tissue | Tissue Distribution in Rats | | | | | | |
|---|---|---|---|---|---|---|---|
| | Time after Dose | | | | | | |
| | 30 min | 1 hr | 4 hr | 6 hr | 24 hr | 48 hr | 72 hr |
| | μg Equivalents of $^{14}C$/g of Tissue | | | | | | |
| Blood (μg/ml) | 0.95 ± 0.05 | 0.43 ± 0.05 | 0.17 ± 0.01 | 0.08 ± 0.01 | 0.00 ± 0.00 | 0.02 ± 0.00 | 0.02 ± 0.00 |
| Plasma (μg/ml) | 0.29 ± 0.02 | 0.12 ± 0.01 | 0.05 ± 0.01 | 0.03 ± 0.00 | 0.01 ± 0.00 | 0.01 ± 0.00 | 0.00 ± 0.00 |
| Heart | 22.04 ± 2.21 | 19.89 ± 1.32 | 16.24 ± 1.52 | 17.85 ± 3.34 | 13.54 ± 0.44 | 14.10 ± 1.41 | 13.80 ± 2.64 |
| Lung | 9.58 ± 1.02 | 8.03 ± 0.57 | 4.32 ± 0.35 | 4.03 ± 0.71 | 1.78 ± 0.16 | 1.60 ± 0.06 | 1.23 ± 0.05 |
| Liver | 7.97 ± 1.35 | 4.05 ± 0.13 | 2.49 ± 0.14 | 1.94 ± 0.02 | 0.83 ± 0.05 | 1.02 ± 0.10 | 0.60 ± 0.06 |
| Pancreas | 13.07 ± 0.73 | 12.68 ± 0.98 | 11.02 ± 1.30 | 10.73 ± 0.81 | 6.83 ± 0.52 | 5.94 ± 0.29 | 1.35 ± 0.53 |
| Spleen | 3.90 ± 0.27 | 2.89 ± 0.16 | 1.69 ± 0.11 | 1.60 ± 0.05 | 0.58 ± 0.08 | 0.31 ± 0.05 | 0.19 ± 0.02 |
| Stomach | 10.05 ± 0.51 | 10.98 ± 1.32 | 9.18 ± 1.18 | 8.41 ± 0.49 | 6.13 ± 0.20 | 6.04 ± 0.41 | 2.89 ± 0.35 |

TABLE 1-continued

| | Tissue Distribution in Rats | | | | | | |
|---|---|---|---|---|---|---|---|
| | Time after Dose | | | | | | |
| Tissue | 30 min | 1 hr | 4 hr | 6 hr | 24 hr | 48 hr | 72 hr |
| Intestine | 30.88 ± 9.36 | 12.56 ± 3.88 | 6.22 ± 1.59 | 3.55 ± 0.41 | 1.66 ± 0.09 | 1.47 ± 0.09 | 0.61 ± 0.09 |
| Kidney | 33.75 ± 1.70 | 27.96 ± 2.58 | 13.68 ± 1.30 | 10.53 ± 1.33 | 5.59 ± 0.35 | 4.94 ± 0.19 | 2.50 ± 0.19 |
| Adrenal | 26.83 ± 2.09 | 23.95 ± 1.41 | 18.66 ± 1.74 | 10.04 ± 1.40 | 5.07 ± 0.72 | 4.79 ± 0.32 | 3.09 ± 0.55 |
| Fat | 0.70 ± 0.12 | 0.95 ± 0.05 | 0.83 ± 0.25 | 0.60 ± 0.06 | 0.35 ± 0.06 | 0.51 ± 0.10 | 0.16 ± 0.01 |
| Testes | 0.37 ± 0.02 | 0.36 ± 0.04 | 0.19 ± 0.02 | 0.19 ± 0.03 | 0.17 ± 0.01 | 0.16 ± 0.01 | 0.17 ± 0.01 |
| Brain | 0.21 ± 0.03 | 0.16 ± 0.01 | 0.08 ± 0.02 | 0.08 ± 0.01 | 0.03 ± 0.01 | 0.02 ± 0.00 | 0.02 ± 0.00 |
| Spinal Cord | 0.23 ± 0.03 | 0.43 ± 0.03 | 0.24 ± 0.02 | 0.18 ± 0.01 | 0.08 ± 0.01 | 0.07 ± 0.00 | 0.07 ± 0.02 |
| Salivary gland | 16.74 ± 2.33 | 10.54 ± 2.01 | 10.64 ± 3.17 | 10.78 ± 2.38 | 9.41 ± 0.74 | 6.46 ± 1.65 | 3.71 ± 0.33 |
| Thyroid | 17.03 ± 1.23 | 33.87 ± 3.20 | 21.40 ± 3.36 | 15.52 ± 2.24 | 8.27 ± 0.57 | 7.43 ± 0.21 | 4.82 ± 1.09 |
| Muscle | 6.07 ± 0.84 | 6.18 ± 0.66 | 5.18 ± 0.75 | 5.54 ± 0.24 | 3.90 ± 0.20 | 5.41 ± 0.59 | 5.36 ± 0.57 |
| Bone | 1.43 ± 0.16 | 1.37 ± 0.03 | 1.03 ± 0.12 | 0.97 ± 0.05 | 0.53 ± 0.03 | 0.33 ± 0.03 | 0.22 ± 0.02 |
| Skin | 1.42 ± 0.11 | 1.49 ± 0.07 | 1.08 ± 0.08 | 1.00 ± 0.10 | 0.64 ± 0.03 | 0.82 ± 0.03 | 0.62 ± 0.04 |
| Eye lens | 0.16 ± 0.03 | 1.15 ± 0.48 | 0.50 ± 0.04 | 0.31 ± 0.23 | 0.03 ± 0.01 | 0.05 ± 0.01 | 0.02 ± 0.01 |

The results of this study suggest that the compounds provided by this invention are highly and selectively bound to heart, kidney, adrenal and thyroid for prolonged periods following administration. Very low levels of compound are bound to the fat, testes, brain or spinal cord, and low levels are observed in the blood or plasma. By six hours following administration of $^{14}$C-clofilium, the ratio of heart to plasma radioactivity was 600. Forty-eight hours after a single 5 mg/kg dose, heart radioactivity levels were more than 700 times greater than whole blood or plasma levels.

The imaging method provided by this invention comprises administering an effective amount of a radioiodinated compound as defined herein and then scanning the area of the body in which the organ to be viewed is located. The scanning is carried out with any commercially available scintiscanning means, for example a standard-field gamma camera equipped with a low-energy, high sensitivity collimeter capable of producing scintigrams. A commonly used radiation detection system for nuclear cardiology is the Anger-type gamma camera. A computerized multi-crystal camera is also routinely employed.

We claim:

1. A method of imaging animal organs comprising administering an effective amount of a compound of the formula

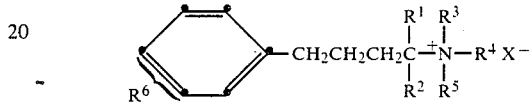

wherein:
 $R^1$ is hydrogen or $C_1$–$C_2$ alkyl;
 $R^2$ is hydrogen or $C_1$–$C_3$ alkyl;
 $R^3$ is $C_1$–$C_4$ alkyl or phenyl-$C_1$–$C_4$ alkyl;
 $R^4$ is $C_1$–$C_8$ alkyl;
 $R^5$ is $C_6$–$C_{10}$ alkyl;
 $R^6$ is a radioiodine atom; and
 X is a therapeutically acceptable anion and scanning the organ region with a scinti-scanning means.

2. The method of claim 1 wherein the organs imaged are heart, kidney, adrenal or thyroid.

3. The method of claim 2 wherein the organ imaged is the heart.

4. The method of claim 3 employing a compound wherein $R^1$ and $R^2$ both are hydrogen.

5. The method of claim 4 employing a compound wherein $R^3$ and $R^4$ both are ethyl.

6. The method of claim 5 employing a compound wherein $R^5$ is n-heptyl.

7. The method of claim 6 employing a compound wherein $R^6$ is 4-$^{123}$I.

8. The method of claim 7 employing a compound wherein X is para-toluenesulfonate.

9. The method of claim 7 employing a compound wherein X is phosphate.

* * * * *